US006635222B2

(12) United States Patent
Kent

(10) Patent No.: US 6,635,222 B2
(45) Date of Patent: *Oct. 21, 2003

(54) METHOD OF STERILIZING PRODUCTS

(75) Inventor: Randall S. Kent, Thousand Oaks, CA (US)

(73) Assignee: Clearant, Inc., Los Angeles, CA (US)

(*) Notice: Subject to any disclaimer, the term of this patent is extended or adjusted under 35 U.S.C. 154(b) by 14 days.

This patent is subject to a terminal disclaimer.

(21) Appl. No.: 09/985,606

(22) Filed: Nov. 5, 2001

(65) Prior Publication Data

US 2003/0059339 A1 Mar. 27, 2003

Related U.S. Application Data

(63) Continuation of application No. 09/570,929, filed on May 15, 2000, now Pat. No. 6,346,216, which is a continuation of application No. 08/573,149, filed on Dec. 15, 1995, now Pat. No. 6,171,549, which is a continuation-in-part of application No. PCT/CA94/00401, filed on Dec. 22, 1994, which is a continuation-in-part of application No. 08/095,698, filed on Jul. 22, 1993, now Pat. No. 5,362,442.

(51) Int. Cl.[7] .............................. A61L 2/08; A01N 1/02
(52) U.S. Cl. .............................. 422/22; 435/2
(58) Field of Search .............................. 422/22; 435/2

(56) References Cited

U.S. PATENT DOCUMENTS

| RE23,195 E | 2/1950 | Brasch |
| 2,832,689 A | 4/1958 | Proctor et al. |
| 2,920,969 A | 1/1960 | Stoddard |
| 2,962,380 A | 11/1960 | Wertheim |
| 3,620,944 A | 11/1971 | Tanito |
| 3,743,480 A | 7/1973 | Falk |
| 3,779,706 A | 12/1973 | Nablo |
| 4,136,094 A | 1/1979 | Condie |
| 4,251,437 A | 2/1981 | Rasmussen et al. |
| 4,282,863 A | 8/1981 | Beigler et al. |
| 4,330,626 A | 5/1982 | Blair et al. |
| 4,336,247 A | 6/1982 | Eriksen |
| 4,370,264 A | 1/1983 | Kotitschke et al. |
| 4,409,105 A | 10/1983 | Hayashi et al. |
| 4,472,840 A | 9/1984 | Jefferies |
| 4,620,908 A | 11/1986 | Van Duzer |
| 4,784,850 A | 11/1988 | Abraham |
| 4,798,611 A | 1/1989 | Freeman, Jr. |
| 4,865,602 A | 9/1989 | Smestad et al. |
| 4,931,361 A | 6/1990 | Baldeschwieler et al. |
| 4,933,145 A | 6/1990 | Uchida et al. |
| 4,946,648 A | 8/1990 | Dichetmëller et al. |
| 4,963,356 A | 10/1990 | Calenoff et al. |
| 5,000,951 A | 3/1991 | Bass et al. |
| 5,012,503 A | 4/1991 | Nambu et al. |
| 5,044,091 A | 9/1991 | Ueda et al. |
| 5,106,619 A | 4/1992 | Wiesehahn et al. |
| 5,134,295 A | 7/1992 | Wälischmiller |
| 5,185,371 A | 2/1993 | Rubinstein |
| 5,226,065 A | 7/1993 | Held et al. |
| 5,283,034 A | 2/1994 | Okrongly et al. ............ 422/22 |
| 5,362,442 A | 11/1994 | Kent |
| 5,418,130 A | 5/1995 | Platz et al. |
| 5,460,962 A | 10/1995 | Kemp |
| 5,510,122 A | 4/1996 | Sreebny et al. |
| 5,548,066 A | 8/1996 | Leneau et al. |
| 5,603,894 A | 2/1997 | Aikus et al. |
| 5,609,864 A | 3/1997 | Shanbrom |
| 5,637,451 A | 6/1997 | Ben-Hur et al. |
| 5,643,464 A | 7/1997 | Rhee et al. |
| 5,712,086 A | 1/1998 | Horowitz et al. |
| 5,730,933 A | 3/1998 | Peterson |
| 5,817,528 A | 10/1998 | Böhm et al. |
| 5,837,313 A | 11/1998 | Ding et al. |
| 5,856,172 A | 1/1999 | Greenwood et al. ......... 435/260 |
| 5,881,534 A | 3/1999 | Ahlqvist et al. |
| 5,981,163 A | 11/1999 | Horowitz et al. |
| 5,986,168 A | 11/1999 | Noishiki |
| 5,989,498 A | 11/1999 | Odland |
| 6,010,719 A | 1/2000 | Remon et al. ............. 424/464 |
| 6,046,024 A | 4/2000 | Burton et al. |
| 6,049,025 A | 4/2000 | Stone et al. |
| 6,060,233 A | 5/2000 | Wiggins ..................... 435/2 |
| 6,066,626 A | 5/2000 | Yew et al. |
| 6,087,141 A | 7/2000 | Margolis-Nunno et al. |
| 6,120,592 A | 9/2000 | Brault et al. |
| 6,159,490 A | 12/2000 | Deghenghi |
| 6,171,549 B1 | 1/2001 | Kent |
| 6,187,572 B1 | 2/2001 | Platz et al. ............. 435/173.3 |
| 6,190,855 B1 | 2/2001 | Herman et al. ............ 435/2 |
| 6,197,207 B1 | 3/2001 | Chapman et al. .......... 435/2 X |
| 6,203,544 B1 | 3/2001 | Gotzen ..................... 606/72 |

(List continued on next page.)

FOREIGN PATENT DOCUMENTS

| CA | 2056619 | 4/1991 |
| CA | 2056619 | 10/1991 |
| EP | 334 679 A2 | 3/1989 |

(List continued on next page.)

OTHER PUBLICATIONS

Patel et al. "Effect of gamma radiation and ethylene oxide on papain," Indian J. Pharm. Sci. (1979), 41(2), pp. 81–83.*

Blanchy, B.B. et al., Immobilization of Factor VIII on Collagen Membranes, J. Biomedical Materials Research, 20:469–479 (1986) (John Wiley & Sons, Inc.).

Borisova, E.A. et al., Protein Degradation During Interphase Death of Thymocytes Induced by Radation and Dexamethasone, pp. 519–521 (1990), abstract.

(List continued on next page.)

Primary Examiner—Elizabeth McKane
(74) Attorney, Agent, or Firm—Fleshner & Kim, LLP

(57) ABSTRACT

A method for sterilizing products to inactivate biological contaminants such as viruses, bacteria, yeasts, molds, mycoplasmas and parasites is disclosed. The method involves irradiating the product at a low dose rate from about 0.1 kGy/hr. to about 3.0 kGy/hr. for a period of time sufficient to sterilize the product. The method does not destroy sensitive materials such as blood and blood components. Further, the method does not require pre-treatment of the product such as freezing, filtration or the addition of chemical sensitizers.

19 Claims, No Drawings

U.S. PATENT DOCUMENTS

| | | | |
|---|---|---|---|
| 6,214,534 B1 | 4/2001 | Horowitz et al. | 435/2 |
| 6,235,508 B1 | 5/2001 | Sowemimo-Coker et al. | 435/173.1 |
| 6,258,821 B1 | 7/2001 | Stogniew et al. | 514/260 |
| 6,346,216 B1 * | 2/2002 | Kent | 422/22 |

FOREIGN PATENT DOCUMENTS

| | | |
|---|---|---|
| EP | 310 316 | 4/1989 |
| EP | 334 679 | 9/1989 |
| EP | 919 918 A3 | 6/1999 |
| EP | 919 918 A2 | 6/1999 |
| JP | 11-216147 | 8/1999 |
| SU | 1321420 A * | 7/1987 |
| WO | WO 90/00907 | 2/1990 |
| WO | WO 91/16060 | 10/1991 |
| WO | WO 95/03071 | 2/1995 |
| WO | WO 00/25839 | 3/2000 |
| WO | WO 01/08611 A1 | 2/2001 |
| WO | WO 01/12318 A1 | 2/2001 |
| WO | WO 01/32107 A2 | 5/2001 |
| WO | WO 01/32110 A2 | 5/2001 |
| WO | WO 01/45720 A1 | 6/2001 |
| WO | WO 01/49219 A1 | 7/2001 |
| WO | WO 01/72233 A1 | 10/2001 |
| WO | WO 01/72244 A1 | 10/2001 |
| WO | WO 01/91818 A1 | 12/2001 |

OTHER PUBLICATIONS

Boyer, T.D. et al., Radiation Inactivation of Mirosomal Glutathione S–Transferase, The Journal of Biological Chemistry, 261:16963–16968 (1986).

Chanderkar, L.P. et al., The Involvement of Aromatic Amino Acids in Biological Activity of Bovine Fibrinogen as Assessed by Gamma–Irradiation, Radiation Research, 65:283–291 (1976) (Academic Press, Inc.).

Chanderkar, L.P. et al., Radiation–Induced Changes In Purified Prothrombin and Thrombin, Biochimica et Biophysica Acta, 706:1–8 (1982) (Elsevier Biomedical Press).

Chin, S. et al., Virucidal Treatment of Blood Protein Products With UVC Radiation, Photochemistry and Photobiology, 65:432–435 (1997) (American Society for Photobiology).

Cornu, O. et al., Effect of Freeze–Drying and Gamma Irradiation on the Mechanical Properties of Human Cancellous Bone, J. Orthopaedic Research, 18:426–431 (2000).

Dyskin, E.A. et al., Hemomicrocirculatory Bed in the Wall of Hollow Organs of the Dog Gastrointestinal Tract at Portal Hypertension, Arkh Anat Gistol Embiol, 93:58–68 (1987).

Dziedzic–Goclawska, A. et al., Effect of Radiation Sterilization on the Osteoinductive Properties and the Rate of Remodeling of Bone Implants Preserved by Lyophilization and Deep–Freezing, Clinical Orthopaedics and Related Research, 272:30–37 (1991).

Ghosh, M.M. et al., A Comparison of Methodologies for the Preparation of Human Epidermal–Dermal Composites, Annals of Plastic Surgery; 39:390–404 (1997) (Lippincott–Raven Publishers).

Hsiue, G. et al., Absorbable Sandwich–Like Membrane for Retinal–Sheet Transplantation, pp. 20–25 (2002 (Wiley Periodicals, Inc).

Jensen, J. et al., Membrane–bound Na, K–ATPase: Target Size and Radiation Inactivation Size of Some of Its Enaymatic Reactions, J. Biological Chemistry, 263:18063–18070 (1988) (Am. Soc. for Biochem. and Mol. Biol.).

Jensen, O. T. et al., Vertical Guided Bone–Graft Augmentation in a New Canine Mandibular Model, The Int'l Journal of Oral and Maxillofacial Implants, 10:335–343 (1995).

Kamat, H.N. et al., Correlation of Structrual Alterations in Bovine Fibrinogen with Loss of Clotting Properties After Gamma Irradiation, Radiation Research, 49:381–389 (1972) (Academic Press, Inc.).

Katz, R.W. et al., Radiation –Sterilized Insoluble Collagenous Bone Matrix is a Functional Carrier of Ostgeogenin for Bone Induction, Calcified Tissue Int., 47:183–185 (1990) (Springer–Verlag New York Inc.).

Kempner, E.S. et al., Effect of Environmental Conditions on Radiation Target Size Analyses, Analytical Biochemistry, 216:451–455 (1994).

Kempner, E.S. et al., Radiation–Damaged Tyrosinase Molecules are Inactive, Biophysical Journal, 55:159–162 (1989) (Biophysical Society).

Kuijpers, A.J. et al. In vivo Compatibility and Degradation of Crosslinked Gelatin Gels Incorporated in Knitted Dacron, pp. 137–144 (2000) (John Wiley & Sons, Inc.).

Le Maire, M. et al., Effects of Ionizing Radiations on Proteins, Journal of Biochem., 267:431–439 (1990).

Ma, J.T. et al., Functional Size Analysis of F–ATPase from *Escherichia coli* by Radiation Inactivation, The Journal of Biological Chemistry, 268:10802–10807 (1993) (The Am. Soc. for Biochem. and Mol. Bio., Inc.).

Marx, G. Protecting Fibrinogen with Rutin During UVC Irradiation for Viral Inactivation, Photochemistry and Photobiology, 63:541–546 (1996) (American Society for Photobiology).

Munting, E. et al., Effect of Sterilization on Osteoinduction, Acta Orthop. Scand., 59:34–38 (1988).

Nagrani, S. et al., The Radiation–Induced Inactivation of External Yeast Invertase in Dilute Aqueous Solution, Int. J. Radiat. Biol., 55:191–200 (1989) (Taylor & Francis Ltd.).

Nielsen, M. et al., The Apparent Target Size of Rat Brain Benzodiazepine Receptor, Acetylcholinesterase, and Pyruvate Kinase Is Highly Influenced by Experimental Conditions, The Journal of Biological Chemistry, 263:11900–11906 (1988) (The American Society for Biochemistry and Molecular Biology, Inc.).

Plavsic, Z. M. et al., Resistance of Porcine Circovirus to Gamma Irradation, BioPharm, pp. 32–36 (Apr. 2001).

Potier, M. et al., Radiation Inactivation of Proteins: Temperature–Dependent Inter–Protomeric Energy Transfer in Ox Liver Catalase, Biochem. J., 298:571–574 (1994).

Prolo, D.J. et al., Composite Autogeneic Human Cranioplasty: Frozen Skull Supplemented With Fresh Iliac Corticocancellous Bone, Neurosurgery, 15:846–851 (1984) (The Congress of Neurological Surgeons).

Puolakkainen, P.A. et al., The Effect of Sterilization on Transforming Growth Factor β Isolated From Demineralized Human Bone, Transfusion, 33:679–685 (1993).

Ripamonti, U. et al., Long–Term Evaluation of Bone Formation by Osteogenic Protein 1 in the Baboon and Relative Efficacy of Bone–Derived Bone Morphogenetic Proteins Delivered by Irradiated Xenogeneic Collagenous Matrices, J. Bone and Mineral Research, 15:1798–1809 (2000) (Am. Soc. for Bone and Mineral Res.).

Sakai, T. et al., Microbiological Studies on Drugs and Their Raw Materials. IV. Sterilization of Microbial Contaminants in Enzyme Powder by Gamma Irradiation, Chem. Pharm. Bull., 26:1130–1134 (1987).

Salehpour, A. et al., Dose–Dependent Response of Gamma Irradiation on Mechanical Properties and Related Biochemical Composition of Goat Bone–Patellar Tendon–Bone Allografts, J. Orthopaedic Research, 13:898–906 (1995).

Salim–Hanna, M. et al., Free Radical Scavenging Activity Of Carnosine, Free Rad. Res. Comms., 14:263–270 (1991) (Harwood Academic Publishers GmbH).

Schwarz, N. et al., Irradiation–sterilization of Rat Bone Matrix Gelatin, Acta Orthop Scand, 59:165–167 (1988).

Smith, C.W. et al., Mechanical Properties of Tendons: Changes With Sterilization and Preservation, J. Biomechanical Engineering, 118:56–61 (1996) (ASME).

Song, K.B. et al., Effect of Gamma–irradiation on the Physicochemical Properties of Blood Plasma Proteins, 2002 Annual Meeting and Food Expo–Anaheim, California, Session 30C–1, Food and Chemistry: Proteins, (Jun. 2002) (Abstract).

Suomela, H., Inactivation of Viruses in Blood and Plasma Products, Transfusion Medicine Reviews, 7:42–57 (1993) (W.B. Saunders Company).

Toritsuka, Y. et al., Effect of Freeze–Drying or γ–Irradiation on Remodeling of Tendon Allograft in Rat Model, J. Orthopaedic Research, 15:294–300 (1997) (Orthopaedic Research Society).

Wangerin, K., et al., Behavior of Differently Sterilized Allogenic Lyophilized Cartilage Implants in Dogs, J. Oral Maxillofac Surg., 45:236–242 (1987).

Wientroub, S. et al., Influence of Irradiation on the Osteoinductive Potential of Demineralilzed Bone Matrix, Calcified Tissue International, 42:255–260 (1988) (Springer–Verlag New York Inc.).

(Abstract of EP0919198A2 and EP0919198A3 (Delphion–DERABS Abstract #G1999–304614)).

Website: www.wslfweb.org/docs/dstp2000.dtopdf/19–MD-.pdf (Defense Science and Technology Plans, (Feb. 2000) p. 176, Section II, MD.03, U.S. Department of Defense Deputy Under Secretary of Defense (Science and Technology)).

Website: www.usacc.org/ataccc/ppt.html, (Advanced Technology Applications for Combat Casualty Care, 2001 Presentations, US Army Medical Research and Material Command Combat Casualty Care Research Program (2001)).

Website: www.usacc.org/RevisedStepB.html, Bakaltcheva, I. et al., (FY01 Request for Proposals–Intramural–Revised 2, Combat Casualty Care Research Program, (2002)).

Website: www.benvue.com/history/history_content.html, (2002).

Website: www.phase–technologies.com/html/vol.2no1.html, Jennings, T.A., (Glossary of Terms for Lyophilization) (1999), abstract.

Website: www.phase–technologies.com/html/vol.1no9.html , Jennings, T.A., (Overview of the Lyophilization Process) (1998), abstract.

Website: www.phase–technologies.com/html/vol.1no2.html , Jennings, T.A., (Role of Product Temperature in the Lyophilization Process) (1988), abstract.

Website: www.phase–technologies.com/html/vol.2no2.html , Jennings, T.A., (What I Wish I Knew About Lyophilization) (1999), abstract.

Website: www.phase–technologies.com/html/vol.1no7.html , Jennings, T.A., (Which Shelf Temperature During Lyophilization?) (1998), abstract.

Website: www.phase–technologies.com/html/vol.1no10.html , Jennings, T.A., (Yes, You have no Eutectic) (1998), abstract.

Ozan Akkus et al., Fracture Resistance of Gamma Radiation Sterilized Cortical Bone Allografts, 2001, pp. 927–934, Journal of Orthopaedic Research, vol. 19.

Tikvah Alper et al., The Exceptionally Small Size of the Scrapie Agent, 1966, pp. 278–284, Biochemical and Biophysical Research Communications, vol. 22, No. 3.

AABB FDA Liaison Meeting, ABC Newsletter, Dec. 12, 1997, pp. 14.

Tikvah Alper et al., Protection by Anoxia of the Scrapie Agent and Some DNA and RNA Viruses Irradiated as Dry Preparations, 1968, pp. 157–166, J. Gen. Virol., vol. 3.

Tikvah Alper et al., Does the Agent of Scrapie Replicate Without Nucleic Acid? May 20, 1967, pp. 764–766, Nature, vol. 214.

Tikvah Alper et al., The Scrapie Agent: Evidence Against its Dependence For Replication on Intrinsic Nucleic Acid, 1978, pp. 503–516, J. Gen. Virol., vol. 41.

S.R. Aparicio et al., Light and Electron Microscopy Studies on Homograft and Heterograft Heart Valves, 1975, pp. 174–162, J. Path, vol. 115.

J. Baksa et al., The Use of Pig's Skin (xenograft) for the Treatment of Burns, 1976, pp. 138–145, Magyar Traumatologin, vol. 19, english abstract.

Michael L. Baldwin et al., Irradiation of Blood Components, 1992, pp. 10–78, American Association of Blood Banks.

R.H. Bassin et al., Abrogation of $Fv-1^b$Restriction With Murine Leukemia Viruses Inactivated by Heat or by Gamma Irradiation, May 1978, pp. 306–315, Journal of Virology, vol. 26, No. 2.

Guy Beauregard et al., Temperature Dependence of the Radiation Inactivation of Proteins, 1985, pp. 117–120, Analytical Biochemistry, vol. 150.

Sandra Blakeslee, Tight Rules on Use of Organs Do Not Apply to Tissues, Jan. 20, 2002. The New York Times Newspaper.

Seymour S. Block, Disinfection, Sterilization, and Preservation, Fundamental Principles of Activity Principles of Antimicrobial Activity, Fourth Edition, 1991, pp. 31–33.

A.J.J.C. Bogers et al., Long–Term Results of the Gamma–Irradiation–Preserved Homograft Monocusp for Transannular Reconstruction of the Right–Ventricular Outflow Tract in Tetralogy of Fallot, 1994, pp. 337–330, Thorac. Cardiovasc. Surgeon, vol. 42.

David R. Brown et al., Antioxidant Activity Related to Copper Binding of Native Prion Protein, 2001 pp. 69–76, Journal of Neurochemistry, vol. 76.

P. Brown, The Risk of Blood–Borne Creutzfeldt–Jakob Disease, 1999, pp. 53–59, Advances in Transfusion Safety Dev. Biol. vol. 102.

P. Brown et al., Further Studies of Blood Infectivity in an Experimental Model of Transmissible Spongiform Encephalopathy, With an Explanation of Why Blood Components Do Not Transmit Creutzfeldt–Jakob Disease in Humans, Nov./Dec. 1999, pp. 1169–1178, Transfusion, vol. 39.

Paul Brown et al., Effect of Chemicals, Heat, and Histopathologic Processing on High–Infectivity Hamster–Adapted Scrapie Virus, May 1982, pp. 683–687, The Journal of Infectious Diseases, vol. 145, No. 5.

P. Brown et al., The Distribution of Infectivity in Blood Components and Plasma Derivatives in Experimental Models of Transmissible Spongiform Encephalopathy, Sep. 1998, pp. 810–816, Transfusion, vol. 38.

D.G. Campbell et al., Sterilization of HIV With Irradiation: Relevance to Infected Bone Allografts, 1999, pp. 517–521, Aust. N.Z.J. Surg., vol. 69.

Ernest U. Conrad et al., Transmission of the Hepatitis–C Virus by Tissue Transplantation, Feb. 1995, pp. 214–224, The Journal of Bone and Joint Surgery, vol. 77–A, No. 2.

A.S. Dagli, Correction of Saddle Nose Deformities by Coral Implantation, 1997, pp. 274–276, Eur. Arch. Otorhinolaryngol, vol. 254.

Defeng et al., Sterilization of Silver–Acidum Pipemedicum Skin for the Treatment of Burns by Radioactive Cobalt–60–.Gamma.–Ray, 1995, pp. 406 (Abstract).

P. Di Simplicio et al., The Reactivity of the SH Group of Bovine Serum Albumin With Free Radicals, 1991, pp. 253–262, Free Rad. Res. Comms., vol. 14, No. 4.

R.J. Donnelly et al., Gamma–radiation of Heart Valves at 4° C; A Comparative Study Using Techniques of Histochemistry and Electron and Light Microscopy, 1973, pp. 95–101, Thorax, vol. 28.

Duane C. Eichler et al., Radiation Inactivation Analysis of Enzymes, Jul. 15, 1987, pp. 9433–9436, The Journal of Biological Chemistry, vol. 262, No. 20.

Luanne H. Elliott et al., Inactivation of Lassa, Marburg and Ebola Viruses by Gamma Irradiation, Oct. 1982, pp. 704–708, Journal of Clinical Microbiology, vol. 16, No. 4.

Bradley M. Fideler et al., Gamma Irradiation: Effects on Biomechanical Properties of Human Bone–Patellar Tendon–Bone Allografts, 1995, pp. 643–646, American Journal of Sports Medicine, vol. 23, No. 5.

Bradley M. Fideler et al., Effects of Gamma Irradiation on the Human Immunodeficiency Virus, Jul. 1994, The Journal of Bone and Joint Surgery, vol. 76–A, No. 7.

Fields et al., Susceptibility of Scrapie Agent to Ionizing Radiation, Apr. 5, 1969, pp. 90–91, Nature, vol. 222.

J.R.P. Gibbons et al., Effects of Gamma Irradiation on the Initial Mechanical and Material Properties of Goat Bone–Patellar Tendon–Bone Allografts, 1991, pp. 209–218, J. Orthop Res, vol. 9, No. 2.

J.R.P. Gibbons et al., Gamma Ray Sterilisation of Homograft Valves, 1969, pp. 353–358, Bulletin De La Societe Internationale De Chirugie, No. 3.

M.J. Goertzen et al., Anterior Cruciate Ligament Reconstruction Using Cryopreserved Irradiated Bone–ACL–Bone–Allograft Transplants, 1994, pp. 150–157, Knee Surgery Sports Traumatology Arthroscopy, vol. 2.

M.J. Goertzen et al., Sterilisation of Canine Anterior Cruciate Allografts by Gamma Irradiation in Argon, Mar. 1995, pp. 205–212, The Journal of Bone and Joint Surgery, vol. 77–B, No. 2.

Slawomir Gregorczyn et al., Strength of Lyophilized and Irradiated Cortical Bone of the Human Femur, 1995, pp. 129–133, Chir. Narz. Ruchu Ortop. Pol., Lx 2, english abstract.

D.A. Haig, Further Studies on the Inactivation of the Scrapie Agent by Ultraviolet Light, 1969, pp. 455–457, J. Gen. Virol., vol. 5.

F.W. Hehrlein et al., Biochemische Veräanderungen an Heterologen Aortenklappentransplantaten nach Anwendung Verschiedener Sterilisationsverfahren, pp. 1183–1185, Langenbecks Arch. Chir., Bd. 325 (Kongrebericht) (English Summary found at page (1183).

F.W. Hehrlein et al., Morphologische Utersuchungen an Heterologen Herzklappentransplantaten Unter Verschiedenen Sterilisationsbedingungen, pp. 244–251 (English Summary found at p. 250), prior art.

H. Hiemstra et al., Inactivation of Human Immunodeficiency Virus by Gamma Radiation and its Effect on Plasma and Coagulation Factors, 1991, pp. 32–39, Transfusion, vol. 31, No. 1.

Richard Hinton et al., A Biomechanical Analysis of Solvent–dehydrated and Freeze–Dried Human Fascia Lata Allografts, 1992, pp. 607–612, The American Journal of Sports Medicine, vol. 20, No. 5.

B. Horowitz et al., Inactivation of Viruses in Labile Blood Derivatives, II. Physical Methods, 1985, pp. 523–527, Transfusion, vol. 25, No. 6.

M. Horowitz, Sterilization of Homograft Ossicles by Gamma Radiation, Nov. 1979, pp. 1087–1089, The Journal of Laryngology and Otology, vol. 93.

Carol House et al., Inactivation of Viral Agents in Bovine Serum by Gamma Irradiation, 1990 pp. 737–740, Can. J. Microbiol., vol. 36.

Shinichiro Ijiri et al., Effect of Sterilization on Bone Morphogenetic Protein, 1994, pp. 628–636, Journal of Orthopaedic Research, vol. 12.

A.S. Imamaliev et al., Biological Properties of Bone Tissue Conserved in Plastic Material and Sterilized With Gama Rays, 1974, pp. 129–135, ACTA, Chirurgiae Plasticae, vol. 16, No. 3.

A. Ingegneri et al., An 11–Year Assessment of 93 Flash–frozen Homograft Valves in the Aortic Position, 1979, pp. 304–307, Thorac. Cardiovasc. Surgeon, vol. 27.

J. Jerosch et al., A New Technique for Bone Sterilization, 1989, pp. 117–120, Biomedizinische Technik, Band 34, Heft 5.

J. Jerosch et al., Influence of Different Rehydration Periods on the Stability and the Water Content of Bone Allografts After Lyophilization, Gamma–Irradiation, and Lipid Extraction, 1994, pp. 335–341, Z. Orthop., vol. 132, engl. abst.

J.D. Keathley et al., Is There Life After Irradiation? Part 2: Gamma–Irradiated FBS in Cell Culture Jul./Aug. 1993, pp. 46–52, BioPharm.

E.S. Kempner et al., Size Determination of Enzymes by Radiation Inactivation, 1979, pp. 2–10, Analytical Biochemistry, vol. 92.

L. Kerboull et al., In Vitro Study of the Influence of Avrious Conservation Methods on the Mechanical Properties of Patellar Tendon Allografts, 1991, pp. 751–762, Chirurgie, vol. 117, english abstract.

A.D. Kitchen, Effect of Gamma Irradiation on the Human Immunodeficiency Virus and Human Coagulation Proteins, 1989, pp. 223–229, Vox Sang, vol. 56.

Andrezej Komender et al., Some Biological Properties of Bovine Trypsinized Fascia Xenografts, 1981, pp. 485–489, Archivum Immunologiae et Therapiae Experimentalis, vol. 29.

Andrezej Komendar et al., Some Biological Properties of Preserved Bovine Fascia Enrighed With Pulverized Calf Cartilage, 1984, pp. 211–219, Archivum Immunologiae et Therapiae Experimentalis, vol. 32.

J.F. Kouvalchouk et al., The Use of Sterilized Bone Allografts in Reconstruction After Tumour Resection, 1986, pp. 393–401, Revue de Chirurgie Orthopedique, vol. 72, english abstract.

Raymond Latarjet, Inactivation of the Agents of Scrapie, Creutzfeldt–Jakob Disease, and Kuru by Radiations, 1979, pp. 387–407, Slow Transmissible Diseases of the Nervous System, vol. 2.

R. Latarjet et al., Inactivation of the Scrapie Agent by Near Monochromatic Ultraviolet Light, Sep. 26, 1970, pp. 1341–1343, Nature, vol. 227.

Douglas C. Lee et al., A Direct Relationship Between the Partitioning of the Pathogenic Prion Protein and Transmissible Spongiform Encephalopathy Infectivity During the Purification of Plasma Proteins, Apr. 2001, pp. 449–455, Transfusion, vol. 41.

Susan F. Leitman, Use of Blood Cell Irradiation in the Prevention of Posttransfusion Graft–vs–Host Disease, 1989, pp. 219–232, Transfus. Sci., vol. 10.

Linberg et al., Irradiated Homologous Cartilage For Orbital Reconstruction, Jul. 1980, pp. 457–462, Ophthalmic Surgery, vol. 11.

Sandra McDowell, Irradiated Cartilage, Spring 1988, pp. 14–15, Plastic Surgical Nursing.

A. Maeda et al., Effects of Solvent Preservation With or Without Gamma Irradiation on the Material Properties of Canine Tendon Allografts, 1993, pp. 181–189, Journal of Orthopaedic Research, vol. 11.

Akira Maeda et al., Solvent–dried and Gamma–irradiated Tendon Allografts in Rats, Jul. 1998, pp. 731–736, The Journal of Bone and Joint Surgery, vol. 80–B, No. 4.

S. Malawski et al., The Use of Dry–Freezed Bone Grafs Sterilized by Gamma Rays in Orthopaedic Surgery, 1969, pp. 61–68, Chir. Narz. Ruchu Ortop, english abstract.

Linda Marton et al., Disinfection and Inactivation of the Human T. Lymphotrogic Virus Type III/Lymphadenopathy–Associated Virus, Aug. 1985, pp. 499–403, The Journal of Infectious Diseases, vol. 151, No. 2.

S.I. Miekka et al., New Methods for Inactivation of Lipid–enveloped and Non–enveloped Viruses, 1998, pp. 402–408, Haemophilia, vol. 4.

Ken Nakata et al., Reconstruction of the Lateral Ligaments of the Ankle Using Solvent–dried and Gamma–Irradiated Allogeneic Fascia Lata, May 2000, pp. 579–582.

Maria Esther Martinez Pardo et al., Clinical Application of Amniotic Membranes on a Patient With Epidermolysis Bullosa, 1999, pp. 68–73, Annals of Transplantation, vol. 4, No. 3–4.

Jan Parizek et al., Duraplasty With Pretreated Freeze–Dried Sterilized Human Dura Mater, 1990, pp. 135–143, Sbor. ved. Praci LF UK Hradee Kralove, vol. 33, english abstract.

Jan Parizek et al., Ovine Pericardium: A New Material For Duraplasty, 1996, pp. 508–513, J. Neurosurg., vol. 84.

L.V. Polezhaeu et al., Repair of Cranial Defects With Regenerating Bone in Grafting Gamma–Irradiated Bone Filings, pp. 57–60.

Pollard, The Effect of Ionizing Radiation on Viruses, pp. 65–71.

Donald J. Prolo et al., Composite Autogeneic Human Cranioplasty: Frozen Skull Supplemental With Fresh Iliac Corticocancellous Bone, Dec. 1984, pp. 846–851, Neurosurgery, vol. 15, No. 6.

Donald J. Prolo et al., Superior Osteogenesis in Transplanted Allogeneic Canine Skull Following Chemical Sterilization, Aug. 1982, pp. 230–242, Clinical Orthopaedics and Related Research, No. 168.

Elena Quaglio et al., Copper Converts the Cellular Prion Protein Into a Protease–resistant Species That Is Distinct From the Scrapie Isoform, Apr. 6, 2001, pp. 11432–11438, The Journal of Biological Chemistry, vol. 276, No. 14.

T.J. Rasmussen et al., The Effects of a 4 Mrad of Gamma–Irradiation on the Initial Mechanical Properties of Bone–Patellar Tendon–Bone Grafts, 1994, pp. 188–197, The Journal of Arthroscoic and Related Surgery, vol. 10, No. 2.

Brian D. Reid, The Sterways Process: A New Approach to Inactivating Viruses Using Gamma Radiation, 1998, pp. 125–130, Biologicals, vol. 26.

S.C. Roe et al., The Effect of Gamma Irradiation on a Xenograft Tendon Bioprothesis, 1992, pp. 149–154, Clinical Materials, vol. 9.

Robert G. Rohwer, Estimation of Scrapie Nucleic Acid MW From Standard Curves for Virus Sensitivity to Ionizing Radiation, Mar. 27, 1986, pp. 381, Nature, vol. 320, No. 6060.

Robert G. Rohwer, Scrapie Infectious Agent is Virus–like in Size and Susceptibility to Inactivation, Apr. 12, 1984, pp. 658–662, Nature, vol. 308.

R.G. Rohwer, The Scrapie Agent: A Virus by Any Other Name, pp. 195–232, Current Topics in Microbiology and Immunology, vol. 172.

Robert G. Rohwer et al., Scrapie–Virus or Viroid, The Case For A Virus, pp. 333–355, Laboratory of Central Nervous System Studies, National Institutes of Neurological and Communicative Disorders and Stroke, National Institutes of Health.

Robert G. Rohwer, Virus–Like Sensitivity of the Scrapie Agent to Heat Inactivation, Feb. 10, 1984, pp. 600–602, Science, vol. 223.

Robert Sullivan et al., Inactivation of Thirty Viruses by Gamma Radiation, Jul. 1971, pp. 61–65, Applied Microbiology, vol. 22, No. 1.

D. Tylman, Mechanical Character of Liofilized and Sterilized by Gamma–Rays Bone Tissue, 1996, pp. 229–234, Chirurgia Narzadow Ruchu I, Ortopedia Polska, english abstract.

W. Welch, A Comparative Study of Different Methods of Processing Aortic Homografts, 1969, pp. 746–749, Thorax, vol. 24.

J.M. White et al., Sterilization of Teeth by Gamma Radiation, Sep. 1994, pp. 1560–1567, J. Dent. Res., vol. 73, No. 9.

Boon–Seng Wong et al., Copper Refolding of Prior Protein, 2000, pp. 1217–1224, Biochemical and Biophysical Research Communications, vol. 276.

Boon–Seng Wong et al., Differential Contribution of Superoxide Dismutase Activity by Prior Protein in Vivo, 2000, pp. 136–139, Biochemical and Biophysical Research Communications, vol. 273.

Boon–Seng Wong et al., Prion Disease: A Loss of Antioxidant Function? 2000, pp. 249–252, Biochemical and Biophysical Research Communications, vol. 275.

D.E. Wyatt et al., Is There Life After Irradiation? Part I: Inactivation of Biological Contaminants, Jun. 1993, pp. 34–39, BioPharm.

Qi Zhang et al., Ethylene Oxide Does Not Extinguish the Osteoinductive Capacity of Demineralized Bone, 1997, pp. 104–108, Acta Orthop Scand, vol. 68, No. 2.

Yongxing Zhang et al., A Comprehensive Study of Physical Parameters, Biomechanical Properties and Statistical Correlations of Iliac Crest Bone Wedges Used in Spinal Fusion Surgery, 1994, pp. 304–308, Spine, vol. 19, No. 3.

License Amendment and procedures for Gamma Irradiation of Blood Products, Jun. 22, 1993, pp. 1–18, Dept. of Health & Human Services, Food and Drug Administration.

M.F. Alladine et al., γ–Radiation Damage to Starr–Edwards Valves, Mar. 16, 1998, pp. 68, The Lancet, Letters to the Editor.

Ch. Baquey et al., Radiosterilization of Albuminated Polyester Prostheses, May 1987, pp. 185–189, Biomaterials, vol. 8.

Edward H. Bedrossian, Jr., HIV and Banked Fascia Lata, 1991, pp. 284–288, Ophthalmic Plastic and Reconstructive Surgery, vol. 7, No. 4.

Liu Bingci, Mouse Antibody Response Following Repetitive Injections of Gamma–Irradiated Human Placenta Collagen, Jun. 1994, pp. 100–103, Chinese Medical Sciences Journal, vol. 9, No. 2.

A.A. Belov et al., The Influence of γ–Radiation on Enzyme Activity of Collalitin in the Process of Storage, Dec. 07, 1989, pp. 519–521, All–Union Research Institute of Textile and Haberdashery Industry, Moscow, engl. abst.

R.G. Burwell, The Fate of Freeze–Dried Bone Allografts, Jun. 1976, pp. 95–111, Transplantation Proceedings, vol. VII, No. 2, Supplement 1.

L. Callegaro et al., Hollow Fiber Immobilized L–Asparaginase: In Vivo and In Vitro Immunological Studies, 1983, pp. 91–96, The International Journal of Artificial Organs, vol. 6, No. 2.

G. Campalani et al., Aortic Valve Replacement With Frozen Irradiated Homografts, 1989, pp. 558–561, Eur. J. Cardio–thoracic Surgery, vol. 3.

David T. Cheung et al., The Effect of γ–Irradiation on Collagen Molecules, Isolated α–chains, and Crosslinked Native Fibers, 1990, pp. 581–589, Journal of Biomedical Materials Research, vol. 24.

David J. Cohen et al., The Fate of Aortic Valve Homografts 12 to 17 Years After Implantation, Mar. 1988, pp. 482–484, Chest, vol. 93, No. 3.

A.G. Churchalin et al., Clinical Immunosorbents Basing On Space–Network Polymers, 1998, pp. 1524–1529, All Union Research Institute of Chemical Reagents and Chemicals of Special Purity, Moscow, engl. abst.

P. De Deyne et al., Some Effects of Gamma Irradiation on Patellar Tendon Allografts, 1991, pp. 51–62, Connective Tissue Research, vol. 27.

R.I. Vaida et al., Structural–Functional Peculiarities of Myocardial Capillaries After Resection of the Lungs, Oct. 21, 1986, pp. 68–73, english abstract.

R. Guidoin et al., A Compound Arterial Prosthesis: The Importance of the Sterilization Procedure on the Healing and Stability of Albuminated Polyester Grafts, Mar. 1985, pp. 122–128, Biomaterials, vol. 6.

Ph. Hernigou et al., Radiation Sterilization of Bone and the HIV Virus, 1993, pp. 445–451, Revue de Chirurgie Orthopedique, vol. 79, english abstract.

Hsing–Wen Sung et al., Effects of Various Chemical Sterilization Methods on the Crosslinking and and Enzymatic Degradation Characteristics of an Epoxy–Fixed Biological Tissue, Dec. 1996, pp. 376–383, Sterilization of Biological Tissues.

James R. Malm et al., An Evaluation of Aortic Valve Homografts Sterilized by Electron Beam Energy, Oct. 1967, pp. 471–477, Journal of Thoracic and Cardiovascular Surgery, vol. 54, No. 4.

James R. Malm et al., Results of Aortic Valve Replacement Utilizing Irradiated Valve Homografts, pp. 740–747, Annals New York Academy of Sciences, prior art.

W. Oh et al., Mitral Valve Replacement With Preserved Cadaveric Aortic Homografts, May 1973, pp. 712–721, The Journal of Thoracic and Cardiovascular Surgery, vol. 65, No. 5.

K. Pietrucha, New Collagen Implant As Dural Substitute, Apr. 1991, pp. 320–323, Biomaterials, vol. 12.

Maria Raptopoulou–Gigi et al., Antimicrobial Proteins in Sterilised Human Milk, Jan. 1, 1977, pp. 12–14, British Medical Journal, vol. 1.

Edward A. Rittenhouse et al., Sterilization of Aortic Valve Grafts for Transplantation, Jul. 1970, pp. 1–5, Aortic Valve Grafts for Transplantation, Archives of Surgery, vol. 101, No. 1.

H. Sato et al., Sterilization of Therapeutic Immunoadsorbents by Ionizing Radiation, 1986, pp. 131–136, The International Journal of Artificial Organs, vol. 9, No. 2.

Richard A. Smith et al., Gamma Irradiation of HIV–1, 2001, pp. 815–819, Journal of Orthopaedic Research, vol. 19.

Barbara Lüssi–Schlatter et al., Die Antimikrobielle Behandlung von Peroralen Enzympräparaten mit Gamma–Strahlen, Pharmazeutisches Institut der Eidgenössischen Technischen Hochschule Zürich Galenische Abteilung, english abstract, prior art.

Martindale's Extra Pharmacopoecia, Glucose p. 1265; prior art.

The Merck Index, Eleventh Edition Glucose pp. 4353–4354, prior art.

G.L. Moore et al., Effects of 4000 Rad. Irradiation on the In Vitro Storage Properties of packed Red Cells, Nov.–Dec. 1985, pp. 583–585, Final Rept., Pub. In Transfusion, vol. 25, No. 6 (Abstract).

Shcheglova et al., The Effect of the Power of Gamma–Radiation on the Radiation Dose in the Sterilization of Drugs, 1984, pp. 730–732, Khim–Farm Zh, vol. 18, No. 6 (Abstract).

G.A. Yarygina, Dose Rate Effect on Survival of Microorganisms Used As Test–Cultures in Radiation Sterilization of Medical Products, 1973, pp. 32–39, Radiats. Tekh., No. 9 (Abstract).

Wyatt et al., "Is There Life After Irradiation? Part 1: Inactivation of Biological Contaminants," Bio. Pharm., Jun. 1993, pp. 34–39.

Wyatt et al., "Is There Life After Irradiation? Part 2: Inactivation of Biological Contaminants," Bio. Pharm., Jul.–Aug. 1993, pp. 46–52.

Leitman, "Use of Blood Cell Irradiation in the Prevention of Posttransfusion Graft–vs–Host Disease" Transfus. Sci., vol. 10, No. 3, 1989, pp. 219–232.

Martindale's Extra Pharmacopoecia, Glucose, p. 1265; prior art.

The Merck Index, Eleventh Edition Glucose pp. 4353–4354, prior art.

"AABB FDA Liaison Meeting," ABC Newsletter, Dec. 12, 1997, p. 14.

Davey "The Effect of Irradiation on Blood Components" Irradiation of Blood Components, Baldwin et al., eds., Bethesda, MD: American Association of Blood Banks, 1992, pp. 51–62.

Defeng et al. "Sterilization of Silver Acidum Pipemedicum Skin for the Treatment of Burns by Radioactive Cobalt–60–Gamma–Ray" Radiat. Phys. Chem., 1995, pp. 643–646.

A.D. Kitchen, G.F. Mann, J.F. Harrison, A.J. Zuckerman. 1989, Effects of Gamma Irradiation on the Human Immunodeficiency Virus and Human Coagulation Proteins, Box Sanguinis, 56: 223–229.

* cited by examiner

METHOD OF STERILIZING PRODUCTS

This application is a continuation of Ser. No. 09/570,929, filed May 15, 2000, and now U.S. Pat. No. 6,346,216, which is a continuation of Ser. No. 08/573,149, filed Dec. 15, 1995, now U.S. Pat. No. 6,171,549, which is a continuation-in-part of PCT/CA94/00401 filed Jul. 22,1994, which is a continuation-in-part of Ser. No. 08/095,698, filed Jul. 22, 1993 now U.S. Pat. No. 5,362,442.

FIELD OF THE INVENTION

The present invention relates to a method for sterilizing products to inactivate biological contaminants such as viruses, bacteria, yeasts, molds, mycoplasmas and parasites.

BACKGROUND OF THE INVENTION

Several products that are prepared for human, veterinary or experimental use may contain unwanted and potentially dangerous contaminants such as viruses, bacteria, yeasts, molds, mycoplasmas and parasites. Consequently, it is of utmost importance that any biologically active contaminant in the product be inactivated before the product is used. This is especially critical when the product is to be administered directly to a patient, for example in blood transfusions, organ transplants and other forms of human therapies. This is also critical for various biotechnology products which are grown in media which contain various types of plasma and which may be subject to mycoplasma or other viral contaminants.

Previously, most procedures have involved methods that screen or test products for a particular contaminant rather than removal or inactivation of the contaminant from the product. Products that test positive for a contaminant are merely not used. Examples of screening procedures include the testing for a particular virus in human blood from blood donors. However, such procedures are not always reliable and are not able to detect the presence of viruses in very low numbers. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the product is contaminated.

More recent efforts have focused on methods to remove or inactivate contaminants in the products. Such methods include heat treating, filtration and the addition of chemical inactivants or sensitizers to the product. Heat treatment requires that the product be heated to approximately 60° C. for about 70 hours which can be damaging to sensitive products. Heat inactivation can destroy up to 50% of the biological activity of the product. Filtration involves filtering the product in order to physically remove contaminants. Unfortunately this method may also remove products that have a high molecular weight. Further, in certain cases small viruses may not be removed by the filter because of the larger molecular structure of the product. The procedure of chemical sensitization involves the addition of noxious agents which bind to the DNA/RNA of the virus and which are activated either by UV or ionizing radiation to produce free radicals which break the chemical bonds in the backbone of the DNA/RNA of the virus or complex it in such a way that the virus can no longer replicate. This procedure requires that unbound sensitizer is washed from cellular products since the sensitizers are toxic, if not mutagenic or carcinogenic, and can not be administered to a patient.

Irradiating a product with gamma irradiation is another method of sterilizing a product. Gamma irradiation is effective in destroying viruses and bacteria when given in high total doses. (Keathly, J. D. Et al.; Is There Life after Irradiation? Part 2; BioPharm July-August, 1993, and Leitman, Susan F.; Use of Blood Cell Irradiation in the Prevention of Post Transfusion Graft-vs-Host Disease; Transfusion Science 10:219–239, 1989). However, the published literature in this area teaches that gamma irradiation can be damaging to radiation sensitive products such as blood. In particular, it has been shown that high radiation doses are injurious to red cells, platelets and granulocytes (Leitman, ibid). Van Duzer, in U.S. Pat. No. 4,620,908 discloses that the product must be frozen prior to irradiation in order to maintain the viability of a protein product. Van Duzer concludes that:

"If the gamma irradiation were applied while the protein material was at, for example, ambient temperature, the material would be also completely destroyed, that is the activity of the material would be rendered so low as to be virtually ineffective."

Unfortunately, many sensitive biologicals, such as blood, would lose viability and activity if subjected to freezing for irradiation purposes and then thawing prior to administration to a patient.

SUMMARY OF THE INVENTION

In view of the above, there is a need to provide a method of sterilizing products that is effective in removing biological contaminants while at the same time having no adverse effect on the product. The present invention has shown that if the irradiation is delivered at a low dose rate, then sterilization can be achieved without harming the product. No prior references have taught or suggested that applying gamma irradiation at a low dose rate can overcome the problems admitted in the prior references.

Accordingly, the present invention provides a method for sterilizing a product comprising irradiating the product with gamma irradiation at a rate from about 0.1 kGy/hr. to about 3.0 kGy/hr. for a period of time sufficient to sterilize the product.

The rate of irradiation can be specifically from about 0.25 kGy/hr. to about 2.0 kGy/hr., more specifically from about 0.5 kGy/hr. to about 1.5 kGy/hr. and even more specifically from about 0.5 kGy/hr. to about 1.0 kGy/hr.

The term "sterilize" as used in the present application generally means to inactivate any biological contaminant present in the product.

The length of time of irradiation or the total dose of irradiation delivered will depend on the bioburden of the product, the nature of the contaminant and the nature of the product.

Higher doses of irradiation are required to inactivate viruses as compared to bacteria. For example, using the dose rates of the present invention, one may use an irradiation time of greater than 10 hours to eliminate viral contamination in contrast to an irradiation time of only 45 minutes to remove bacterial contamination.

The process according to the present invention can be carried out at ambient temperature and does not require the heating, freezing, filtration or chemical treatment of the product before the process is carried out. This offers another significant advantage of the present process as it avoids some of the extra treatment steps of the prior art processes.

Certain products, such as blood, may be diluted prior to irradiation. Diluting the product may serve to reduce degradation of the product during irradiation. The choice of diluent depends on the nature of the product to be irradiated. For example, when irradiating blood cells one would choose a physiologically acceptable diluent such as citrate phosphate dextrose.

In cases where living cells (such as blood cells) are to be irradiated, a scavenger may be added to bind free radicals and other materials that are toxic to cells. A suitable scavenger is ethanol.

The efficacy of the method of the present invention is contrary to what others skilled in this area have observed or predicted. (U.S. Pat. No. 4,620,908 and Susan Leitman, ibid). The method provides a method of irradiating products that is not harmful to the product itself. In particular, the method of the present invention can effectively sterilize a product as fragile as blood without destroying the viability of the cells contained therein. Consequently the method of the present invention offers a significant technical and scientific advancement to the sterilization field. The method also provides an invaluable service to health care and the general public by providing a method to produce safe and sterile products for human use. This is especially critical in light of the spread of viral diseases such as AIDS and hepatitis through the transfusion of contaminated blood and blood products.

DESCRIPTION OF PREFERRED EMBODIMENTS

The following examples are provided in order to illustrate the method of the present invention and are not meant to limit the scope of the invention.

EXAMPLE 1

Sterilization of Blood

A 200 ml bag of one day old packed red blood cells was used. Ethanol was added to the cells in order to achieve a final ethanol concentration of 0.01% v/v. The red blood cells were diluted by a factor of one in ten using a modified Citrate Phosphate Dextrose (CPD) solution having a pH of about 6.4 to 6.7 and having the following composition in a total volume of 500 ml:

| | |
|---|---|
| Citric Acid Monohydrate | 0.2 g |
| Sodium Citrate Dihydrate | 26.3 g |
| Sodium Monobasic Phosphate | 2.2 g |
| Sodium Dibasic Phosphate | 1.0 g |
| Dextrose | 3.2 g |

The cells were irradiated in a commercial size gamma irradiator which contained a cobalt 60 source rack. Irradiation was done off carrier in an unprotected box. The cells were irradiated for twenty four hours at a rate of approximately 1 kGy/hr. After the irradiation period the red blood cells were examined visually and were found to be viable, having a brilliant red colour. A control sample, consisting of packed red blood cells that were not diluted with the above-described CPD solution, was not viable after irradiation.

Four days after the irradiation procedure, the diluted cells were tested for levels of various blood components and the results are shown in Table 1. The control sample consisted of blood from the same bag as the test sample but it did not undergo irradiation. Table 1 illustrates that dilution and irradiation of human blood cells did not significantly alter the white blood cell count. The platelet count and hematocrit values were slightly lower than the control; however, these values are still within the range that is seen in normal adult blood. The level of hemoglobin was higher than in the control indicating that some red blood cells did lyse during the procedure. This is also evidenced by the lower red blood cell count. Nevertheless, contrary to what has been previously published, up to 25 kGy of radiation did not destroy the components of blood by the present procedure. The cells were also counted and found to be viable after 25 kGy of gamma irradiation delivered at a low dose rate of 1 kGy/hr.

TABLE 1

| Component | Irradiated Blood | Control Blood |
|---|---|---|
| White Blood Cells | 4 K/mm$^3$ | 4.8 K/mm$^3$ |
| Red Blood Cells | 3 Mi/mm$^3$ | 7.2 Mi/mm$^3$ |
| Hemoglobin | 42 g/dl | 21 g/dl |
| Hematocrit | 46% | 64% |
| Platelet | 100 k/mm$^3$ | 120 k/mm$^3$ |

EXAMPLE 2

Sterilization of Dextrose

Dextrose (or glucose) containing solutions are used in the treatment of carbohydrate and fluid depletion, in the treatment of hypoglycaemia, as a plasma expander, in renal dialysis and to counteract hepatotoxins (The Merck Index, Eleventh Edition; Merck & Co. Inc., 1989 and Martindale's Extra Pharmacopecia p. 1,265). Dextrose is also the preferred source of carbohydrate in parental nutrition regimens (The Merck Index, Eleventh Edition; Merck & Co. Inc., 1989 and Martindale's Extra Pharmacopecia p. 1,265). In all of the above applications, the dextrose must be sterilized before use. Sterilization of dextrose containing products is generally done by heat sterilization or autoclaving. Unfortunately, these methods have been reported to degrade or caramelize dextrose containing solutions resulting in a colour change in the solution (Martindale's Extra Pharmacopecia p. 1,265). Gamma irradiation of glucose has also been reported to decompose glucose containing solutions (Kawakishi et al.; Radiation-Induced Degradation of D-glucose in Anaerobic Condition. Agric. Biol. Chem. June, 1977). Therefore, there is a need for a method that can sterilize dextrose containing products that does not degrade the product itself. In view of the problems of the prior art, a dextrose solution was treated according to the method of the present invention as follows.

A 5% dextrose solution was irradiated for 24 hours, at a rate of approximately 1 kGy/hr. After irradiation the product was tested and it was found that there was no visible light spectrum change as compared to the non-irradiated control. Therefore, the present method can be useful in sterilizing products that contain dextrose.

In addition to the above experiment, fresh solutions of 5% and 50% dextrose were irradiated to 25 kGy over 36 hours at ambient temperature. The results were similar to those described above. In addition, UV/VIS scans were obtained and demonstrated a complete absence of the peak at 283.4 nm for "furfurals" as per U.S.P. In contrast, dextrose samples sterilized using an autoclave contain the 283.4 furfural peak. "Furfurals" are carcinogenic.

EXAMPLE 3

Sterilization of Human Serum Albumin

Normal Human Serum Albumin was irradiated as a 25% salt-poor solution to a total dose of 25 kGy over 36 hours using a Gammacell 220 ($Co^{60}$ is the gamma ray source in this instrument). The temperature was not controlled during the irradiation but it is estimated that the container holding the albumin solution was approximately 23° C. The results of HPLC analysis are given in Table 2.

TABLE 2

| PARAMETER | CONTROL (%) | IRRADIATED (%) |
|---|---|---|
| Polymer | 2 | 3 |
| Dimer | 7 | 8 |
| Monomer | 90 | 86 |
| Low Molecular Weight | 1 | 3 |
| pH | 7.05 | 6.97 |
| NTU (must be >20) | 11.4 | 11.4 |

As the results demonstrate, Normal Human Serum Albumin can safely be irradiated to 25 kGy (at a rate of approximately 0.7 kGy/hr.) at room temperature without adversely affecting the essential properties of the protein. This has not been demonstrated before. All other attempts at irradiating serum albumin require that it be irradiated in the frozen stage. This adds to the cost and difficulty of doing the irradiation.

EXAMPLE 4

Normal human blood from a healthy donor was taken in a heparinized tube, washed three times with standard CPD solution, then diluted 1:20 with CPD containing 0.01% v/v Ethanol. This latter solution of CPD with 0.01% v/v Ethanol is called SCPD. Two ml aliquots were then placed in 10 ml plastic test tubes and irradiated to different doses up to 26 kGy over 36 hours at room temperature. There was no haemolysis and the cells appeared intact if somewhat large and slightly irregular in shape. The results of three separate experiments are reported in Table 3.

experiments, the cells were gently agitated after 12, 16 and 24 hours of irradiation. Further, in the third experiment, (Example 7), the cells were placed in T25 flasks to provide greater surface area and reduce the concentration due to settling in the bottom of the centrifuge tubes. In each case, the cells were irradiated at a dose rate of approximately 0.7 kGy/hr.

EXAMPLE 5

Sterilization of HIV-containing Blood

The following experiment was undertaken with the following specific objectives:

1. To evaluate the toxicity of the process towards red blood cells (RBCs).
2. To evaluate the anti-retroviral activity of the process.

Procedure

Initially, 2 ml of anticoagulated-blood was obtained from an HIV-seronegative donor. The blood was centrifuged, and the plasma was removed. The remaining cell pellet was resuspended in 10 ml of the CPD buffer and centrifuged. This washing process was repeated a total of three times. The final pellet was resuspended in 40 ml of the SCPD buffer, and distributed into plastic tubes in 2 ml aliquots, with 16 separate aliquots being retained for further manipulation. For 8 of these tubes, an aliquot of HTLV-IIIB was added. This is a laboratory strain of the HIV virus and 100 tissue culture infective doses (TCID) were added to each of the tubes to be infected. For the remaining 8 tubes, a "mock" infection was performed, by adding a small amount of non-infectious laboratory buffer, phosphate buffered saline (PBS). Four infected and four non-infected tubes were subjected to the process. For comparison, the remaining 8 tubes (four infected and four non-infected) were handled in an identical manner, except that they were not subjected to the process.

TABLE 3

| PARAMETER | RBC[1] | HGB[2] | HCT[3] | MCV[4] | MCH[5] | MCHC[6] | RDW[7] | FLAGS |
|---|---|---|---|---|---|---|---|---|
| 1* | 1.08 | 41 | .097 | 89.5 | 38.3 | 427 | 17.7 | Nearly Normal |
| CONTROL | .99 | 33 | .089 | 90.2 | 33.0 | 366 | 15.3 | |
| 2* | | | | 95.0 | 32.3 | 339 | 12.0 | |
| 12 kGy 1 | 1.22 | 45 | .166 | 135.8 | 36.5 | 269 | 27.3 | 1 + Anisocytosis |
| | 1.38 | 45 | .199 | 144.7 | 33.0 | 228 | 24.9 | 3 + Macrocytocis |
| 1 | 1.04 | 32 | .169 | 163.0 | 31.3 | 192 | 18.8 | 1 + Anisocytosis |
| 16 kGy | 0.54 | 29 | .088 | 162.5 | 54.5 | 335 | 18.8 | 3 + Macrocytocis |
| 2 | 0.82 | 27 | .128 | 156.5 | 32.8 | 209 | 19.8 | 2 + Anisocytosis |
| | 0.81 | 26 | .124 | 152.6 | 32.4 | 212 | 20.2 | 3 + Macrocytocis |
| 1 | 0.79 | 244 | .125 | 158.4 | 30.8 | 194 | 19.4 | 1 + Anisocytosis |
| 20 kGy | 1.26 | 28 | .203 | 161.5 | 22.1 | 137 | 19.0 | 3 + Macrocytocis |
| 2 | 0.93 | 30 | .141 | 151.5 | 32.3 | 213 | 20.1 | 2 + Anisocytosis |
| | 0.92 | 30 | .143 | 155.5 | 32.1 | 207 | 20.5 | 3 + Macrocytocis |
| 26 kGy 1 | 1.15 | 34 | .180 | 155.9 | 29.4 | 189 | 19.3 | 1 + Anisocytosis |
| | 1.15 | 34 | .176 | 153.0 | 29.9 | 195 | 23.4 | 3 + Macrocytocis |

*Experiment 1 and Experiment 2
[1]Red Blood Cell Count: Cells × $10^{12}$/liter
[2]Hemoglobin: grams/liter
[3]Hematocrit
[4]Mean Corpuscular Volume: Femtoliters
[5]Mean Corpuscular hemoglobin: picograms
[6]Mean Corpuscular hemoglobin Concentration: grams/liter The cells were easily put into suspension and reconstituted in fresh buffer.

The following three experiments (Examples 5, 6 and 7) were conducted in order to determine the efficacy of the method when treating HIV-contaminated blood. In each Example the cells were similarly treated. In these It should be stated that at the beginning of the study, a separate aliquot of blood was obtained from the donor. This was processed in the clinical hematology laboratory and a complete hemogram was performed. These baseline results were compared to repeat testing on the study aliquots, which included evaluation of four processed and four unprocessed samples, all of which were not infected with HIV.

An aliquot of 0.5 ml of each of the infected study samples was inoculated on mononuclear cells (MCs) which had been obtained three days earlier. These cells had been suspended in RPMI culture medium, with 10% fetal calf serum and other additives (penicillin, streptomycin, glutamine and HEPES buffer) along with 1 ug/ml PHA-P. At the same time as this inoculation, the cells were resuspended in fresh medium with rIL-2 (20 U/ml). The cultures were maintained for 7 days. Twice weekly, a portion of the culture medium was harvested for the measurement of HIV p24 antigen levels (commercial ELISA kit, Coulter Electronics, Hialeah, Fla.) for the measurement of viral growth.

A separate aliquot of the eight infected study samples was used for viral titration experiments. Briefly, serial four-fold dilutions of the virus-containing fluids (ranging from 1:16 to 1:65,536) were inoculated in triplicate in 96-well flat-bottom tissue culture plates. PHA-stimulated MCs were added to each well (4 million cells in 2 ml culture medium, with IL-2). An aliquot of the supernatant from each culture well was harvested twice weekly for the measurement of HIV p24 antigen levels. A well was scored as "positive" if the HIV p24 antigen value was >30 pg/ml.

The viral titer was calculated according to the Spearman-Karber method (see ACTG virology protocol manual) using the following equation:

$$M = xk + d[0.5 - (1/n)r]$$

M: titer (in log 4)
xk: dose of highest dilution
d: space between dilutions
n: number of wells per dilution
r: sum of total number of wells Results Red blood cell parameters for the baseline sample as well as for the unprocessed and processed study samples are shown in Table 4.

TABLE 4

| Sample/Number | MCV | MCH | MCHC |
|---|---|---|---|
| Baseline | 94.5 | 32.0 | 339 |
| Unprocessed-1 | 91.4 | 34.4 | 376 |
| Unprocessed-2 | 90.2 | 37.9 | 420 |
| Unprocessed-3 | 92.1 | 40.0 | 433 |
| Unprocessed-4 | 91.0 | 40.2 | 442 |
| Processed-1 | 133.4 | 37.8 | 284 |
| Processed-2 | 131.5 | 45.0 | 342 |
| Processed-3 | 128.5 | 38.9 | 303 |
| Processed-4 | 131.1 | 39.4 | 301 |

The abbreviations used in Table 4 are explained under Table 3.

As described above, HIV cultures were established using 0.5 ml aliquots of unprocessed and processed study samples. P24 antigen levels (pg/ml) from the study samples on day 4 and day 7 of culture are shown in Table 5.

TABLE 5

| Sample/Number | p24-DAY 4 | p24-DAY 7 |
|---|---|---|
| Unprocessed-1 | 1360 | 464 |
| Unprocessed-2 | 1180 | 418 |
| Unprocessed-3 | 1230 | 516 |
| Unprocessed-4 | 1080 | 563 |
| Processed-1 | 579 | 241 |
| Processed-2 | 760 | 303 |
| Processed-3 | 590 | 276 |
| Processed-4 | 622 | 203 |

Finally, one unprocessed sample and one processed sample were selected for the performance of direct viral titration without culture. The results are shown in Table 6.

TABLE 6

| Sample/Number | Titer (log 10 ml) |
|---|---|
| Unprocessed-1 | 1.5 |
| Processed-1 | 0.0 |

The red blood cells were minimally affected by the process, although some reproducible macrocytosis was observed. Although on co-culturing of processed samples, there appeared to be some residual live virus, this was not confirmed by direct titration experiments.

EXAMPLE 6

The objective of this experiment was to evaluate the toxicity of the process towards red blood cells in a comprehensive manner.

Methods

For this experiment, 1 ml of anticoagulated blood was obtained from the same HIV-seronegative donor as in the first experiment. The blood was centrifuged and the plasma was removed. The remaining cell pellet was resuspended in 10 ml of the CPD buffer and centrifuged. This washing process was repeated a total of three times. The final pellet was resuspended in 20 ml of the SCPD buffer, and distributed into plastic tubes in 2 ml aliquots, with all 10 aliquots being retained for further manipulation. Eight tubes were subjected to the process, while the final two tubes were retained as control, unprocessed tubes. After the processing, all ten tubes were centrifuged, and the resulting pellet was resuspended in 100 ul buffer. A complete hemogram was performed on these reconcentrated study samples.

As in the first experiment, a separate aliquot of blood was obtained from the donor when the study sample was taken. A complete hemogram was performed on this baseline sample. As the study samples were re-concentrated to 33–50% of their original state, more direct comparisons with the baseline sample could be undertaken than were possible in our earlier experiment.

Results

Red blood cell parameters for the baseline sample as well as for the unprocessed and processed study samples are shown in Table 7. The abbreviations used in Table 7 are defined in Table 3.

TABLE 7

| Sample/Number | RBC | HGB | MCV | MCH | MCHC |
|---|---|---|---|---|---|
| Baseline | 4.76 | 152 | 94.9 | 31.9 | 336 |
| Unprocessed-1 | 0.99 | 33 | 90.2 | 33.0 | 366 |
| Unprocessed-2 | 1.08 | 41 | 89.5 | 38.3 | 427 |
| Processed-1 | 1.15 | 34 | 153.0 | 29.9 | 195 |
| Processed-2 | 1.15 | 34 | 155.9 | 29.4 | 189 |
| Processed-3 | 1.26 | 28 | 161.5 | 22.1 | 137 |
| Processed-4 | 0.79 | 24 | 158.4 | 30.8 | 194 |
| Processed-5 | 0.54 | 29 | 162.5 | 54.5 | 335 |
| Processed-6 | 1.04 | 32 | 163.0 | 31.3 | 192 |
| Processed-7 | 1.35 | 45 | 144.7 | 33.0 | 228 |
| Processed-8 | 1.22 | 45 | 135.8 | 36.5 | 269 |

There was macrocytosis of the cells which was present in all the processed samples. Comparable hemoglobin levels were measured in the unprocessed and processed samples. The absolute values were appropriate for the residual dilution. The red blood cells are preserved.

EXAMPLE 7

The objective of this experiment was to verify and expand upon the results obtained in Example 6.

Methods

For this experiment 5 ml of anticoagulated blood was obtained from the same HIV-seronegative donor as in the first two experiments. The blood was centrifuged, and the plasma was removed. The remaining cell pellet was resuspended in 100 ml of the CPD buffer, and centrifuged. This washing process was repeated a total of three times. The final pellet was resuspended in 100 ml of the SCPD buffer, and distributed in 25 ml aliquots, in T25 tissue culture flasks, with all four aliquots been retained for further manipulation. Two flasks were subject to the process, while the other two were retained as control, unprocessed flasks. After the processing, the contents of each of the flasks was observed and a visual determination of the cells capacity to absorb oxygen (turning a brighter red on exposure to ambient air) was made. Following this, the contents of the flasks were aspirated and centrifuged, with the residual pellet resuspended in a small volume of buffer. A complete hemogram was performed on these re-concentrated study samples.

As in Examples 5 and 6, a separate aliquot of blood was obtained from the donor when the study sample was taken. A complete hemogram was performed on this baseline sample. As the study samples were re-concentrated to 33–50% of their original state, direct caparisons of a number of specific parameters would be possible with the baseline sample.

Results

On visual inspection, there were no appreciable differences between the processed and unprocessed study samples. Specifically, there appeared to be a uniform distribution of well suspended cells. On exposure to ambient air, the contents of all flasks became somewhat brighter red. No specific quantitative measurements of oxygenation were made.

Red blood cell parameters for the baseline sample as well as for the unprocessed and processed study samples are shown in Table 8. The abbreviations used in Table 8 are defined under Table 3.

TABLE 8

| Sample/Number | RBC | HGB | MCV | MCH | MCHC |
|---|---|---|---|---|---|
| Baseline | 4.75 | 153 | 95.0 | 32.3 | 339 |
| Unprocessed-1 | 0.93 | 30 | 151.5 | 32.3 | 213 |
| Unprocessed-2 | 0.92 | 30 | 155.5 | 32.1 | 207 |
| Processed-1 | 0.82 | 27 | 156.5 | 32.8 | 209 |
| Processed-2 | 0.81 | 26 | 152.6 | 32.4 | 212 |

This experiment was designed to more closely approximate conditions of red blood cells to be transfused into a patient, and was consequently conducted at higher volumes. On a preliminary basis, it does not appear that the process impairs the red blood cells' ability to carry oxygen, although this should be measured more formally. Interestingly, in this experiment, there was no difference in cell size between the processed and unprocessed samples, both being large compared to baseline. Comparable haemoglobin levels were measured in all the study samples.

EXAMPLE 8

In this experiment, Immunoglobulin G (IgG) was irradiated in lyophilized form.

Method

The IgG was irradiated as a powder to a total dose of 25 kGy using a Gammacell 220. The temperature of the container holding the material was approximately 23° C. The dose rate was 0.72 kGy/hr.

Results

The results of HPLC analysis of IgG are given in Table 9. As the results demonstrate, the product appears to be unaffected after being irradiated to a dose of 25 kGy at room temperature when the irradiation is delivered at a rate of approximately 0.7 kGy/hr. This has not been previously demonstrated.

TABLE 9

| PARAMETER | CONTROL (%) | IRRADIATED (%) |
|---|---|---|
| Polymer (must be >2%) | 1 | 1 |
| Dimer | 10 | 13 |
| Monomer | 88 | 84 |
| Low Molecular Weight | 1 | 2 |

The results presented by Gergely, et al. using freeze dried IgG showed that a portion of the protein was insoluble after an irradiation dose of 12 kGy to 25 kGy at standard irradiation dose rates. (Gergely, J., Medgyesi, G. A., Igali, A. Studies of Gamma-Ray-Irradiated Human Immunoglobulin G. SM-92/12 I.A.E.A.). These results would indicate a change/degradation of the protein. In contrast, using the present method at a dose rate of approximately 0.7 kGy/hr., none of the protein was insoluble. This would indicate that little or no change or degradation of the protein occurred. Further, Gergely et al. found that a liquid formulation of human IgG lost all of its activity after irradiation. In studies using the present method on intravenous immunoglobulin (IVIG) in liquid form, it was shown that greater than 70% of a specific antibody in hyperimmune IVIG was retained.

EXAMPLE 9

In this experiment, alpha 1 proteinase inhibitor and fibrinogen were irradiated in lyophilized form.

Method

The samples were placed in a Gammacell 220 and irradiated according to the present process to a total dose of 25 kGy. Samples were then returned to the laboratory for analysis. The dose rate was 0.72 kGy/hr.

Results

The alpha 1 proteinase inhibitor, both treated and control, were 40% of a standard normal pooled plasma sample. The Mancini radial immunodiffusion technique was used as the assay.

The topical fibrinogen complex vials were reconstituted in 10 ml of water. Protamine sulphate at a concentration 10 mg/ml was added to the samples. There was instant formation of monomer in all three preparations.

EXAMPLE 10

In this experiment, Factors VII, VIII and IX were irradiated in lyophilized form.

Method

The samples were placed in a Gammacell 220 and irradiated to various total doses at a dose rate of approximately 1 kGy/hr.

Results

Factor VII retained 67% activity at 20 kGy and 75% at 10 kGy. Factor VIII retained 77% activity at 20 kGy and 88% at 10 kGy. Similarly Factor IX showed an activity level of 70% at 20 kGy and 80% at 10 kGy.

Analysis

Excellent results were found for the three Factors. To our knowledge, no one has been able to achieve these results by irradiating the Factors at ambient temperature to such a high dose of radiation with such little loss of activity. This is in direct contrast with the results of Kitchen et. al. (Kitchen, A. D. Mann, G. F., Harrison, J. F., Zuckerman, A. J. Effect of Gamma Irradiation on the Human Immunodeficiency Virus and Human Coagulation Proteins. Vox Sang 1989, 56:223–229) who found that "the irradiation of lyophilized concentrates is not a viable procedure". Similarly, Hiemstra et. al., (Hiemstra, H., Tersmette, M., Vos., A. H. V., Over, J., van Berkel, M. P. and de Bree, H. Inactivation of human immuondeficiency virus by gamma radiation and its effect on plasma and coagulation factors. Transfusion, 1991, 31:32–39) also concluded that "Gamma radiation must be disregarded as a method for the sterilization of plasma and plasma-derived products, because of the low reduction of virus infectivity at radiation doses that still give acceptable recovery of biologic activity of plasma components."

EXAMPLE 11

In this experiment, red blood cells were irradiated at a dose rate of 0.5 kGy/hr. for periods of time ranging from 7 ½ to 90 minutes in order to remove bacterial contaminants.

Method

Red blood cells were collected from a healthy donor in EDTA, washed 3 times with CPD solution and resuspended in CPD to provide a 1:20 dilution based on the original blood volume. The cell suspension was then subdivided into 14 tubes. To seven of the tubes approximately $1.0 \times 10^4$ Staphylococcus epidermidis were added. The cells were placed on ice for transport to the irradiation facility. All of the samples were placed in the chamber at ambient temperature and irradiated at 0.5 kGy/hr. for periods of time to give total doses of 0.0625, 0.125, 0.250, 0.375, 0.500 and 0.750 kGy respectively. The samples were removed and agitated at each time point and placed on ice for transport either to the microbiology lab or to the hematology lab for analysis.

Results

The results of the microbiology assays are given in Table 10.

TABLE 10

| RADIATION DOSE (kGy) | TIME (MIN) | NUMBER SURVIVING |
|---|---|---|
| 0 | | 92200 |
| 0.0625 | 7.5 | 84500 |
| 0.125 | 15 | 35000 |
| 0.250 | 30 | 10067 |
| 0.375 | 45 | 1800 |
| 0.500 | 60 | 250 |
| 0.750 | 90 | 0 |

Thus a dose of 0.75 kGy provides a 4.5 $\log_{10}$ reduction in bacterial survivors. This represents a significant safety factor for blood. Further, the $D_{10}$ value is approximately 0.125 kGy which corresponds well with the values reported in the literature for similar species of staphylococcus (B. A. Bridges, The effect of N-Ethylmaleimide on the radiation sensitivity of bacteria. J. Gen. Microbiol. 1961, (26) 467–472 and G. P. Jacobs and N. Sadeh, Radiosensitization of Staphylococcus aureus by p-hydroxybenzoic acid. Int. J. Radiat. Biol; 1982, 41, 351–356).

In order to demonstrate that the red blood cells remained viable after the irradiation process, the following parameters were determined for the cells; WBC, Neutrophils, Lymphocytes, Monocytes, Eosinophils and Basophils. These determinations merely enumerated the number of cells present. All nucleated cells would, of course, be inactivated by the radiation dose delivered. The other red blood cell parameters monitored are listed in Table 11. The Methaemoglobin value was unchanged from that of the controls even after a radiation dose of 0.75 kGy. This experiment demonstrates that red blood cells can be safely irradiated by the present method to a dose of 0.75 kGy at room temperature with no loss of cell function.

Red Blood Cell Values as a Function of Radiation Dose Received

TABLE 11

| Parameter | Whole Blood | Total Dose (In kGy) | | | | |
|---|---|---|---|---|---|---|
| | | 0 | 0.0625 | 0.125 | 0.250 | 0.500 |
| RBC | 5.06 | 1.49 | 1.27 | 1.77 | 1.73 | 1.43 |
| HGB | 153 | 43 | 41 | 56 | 56 | 46 |
| HCT | .483 | .142 | .120 | .167 | .163 | .131 |
| MCV | 95.5 | 95.6 | 94.3 | 94.2 | 93.7 | 92.1 |
| MCH | 31.2 | 31.1 | 32.2 | 31.7 | 32.2 | 32.5 |
| MCHC | 327 | 325 | 341 | 336 | 344 | 353 |
| RDW | 13.3 | 12.1 | 12.7 | 12.9 | 12.9 | 13.2 |
| METHgB | 0.9 | 0.3 | 0.3 | 0.3 | 0.0 | 0.9 |

EXAMPLE 12

This experiment was conducted using the method in Example 11 to confirm the findings of Example 11 and to expand upon some of the parameters measured. The results of this experiment are given in Table 12.

Results
Red Blood Cell Values as a Function of Radiation Dose Received

TABLE 12

| | Total Dose (In kGy) | | | | | | |
|---|---|---|---|---|---|---|---|
| PARAMETER | 0 | 0.0625 | 0.125 | 0.250 | 0.375 | 0.555 | 0.750 |
| HGB | 1.8 | 1.7 | 1.8 | 1.7 | 2.0 | 2.0 | 2.0 |
| % O | 96.6 | 96.5 | 96.2 | 96.3 | 96.4 | 96.5 | 96.0 |
| % CO | 1.0 | 1.2 | 1.6 | 1.3 | 1.7 | 1.5 | 1.5 |
| % MET | 0.5 | 0.5 | −0.5 | 0.4 | −0.2 | 0.4 | 0.8 |
| % REDUCED | 1.9 | 1.9 | 2.7 | 2.2 | 2.2 | 1.7 | 1.7 |
| p60 (mm Hg) | 34 | nd | nd | nd | nd | nd | 24 |
| Hill Coefficient | 2.1 | nd | nd | nd | nd | nd | 1.8 | nd = not done
The uncertainty with the methaemoglobin levels is ± 2%; with p50 it is ± 4% (95% confidence).

These results confirm the previous results and indicate that indeed, red blood cells can be irradiated to a dose sufficient to provide 4.5 $\log_{10}$ (reduction in bacteria count.

It is contemplated that future experiments will provide similar results for platelets. Thus with little or no additional manipulation, and without the addition of extraneous materials, red blood cells can be treated by the present process to provide a bacteriologically safe product, thus further reducing the risk of untoward reactions in recipients.

As evidenced by all of the above experiments, the present invention demonstrates that irradiating a product at a low dose rate from about 0.1 kGy/hr. to about 3.0 kGy/hr. is effective in sterilizing the product without adversely affecting the product itself.

While the Examples relate to specific embodiments of the method of the present invention, one skilled in the art will realize that the total time of irradiation will depend on the type of contaminant, the bioburden of the product and the nature of the product. For example, bacterial contaminants can be eliminated with very little irradiation time while viral inactivation requires a longer irradiation time. Further, extremely sensitive products, such as blood, are preferably diluted in a physiologically acceptable diluent prior to irradiation.

It is to be appreciated that the method of the present invention can be used to treat an extremely wide variety of products that require sterilization. The fact that the present method has proven effective in blood which is a fragile biological material makes it reasonable to predict that the method can be used on many similarly sensitive products. Examples of other products that may be treated include pharmaceuticals, proteins, nucleic acids, blood components, body fluids (such as cerebral spinal fluid, saliva), liposomes, glucose containing products, cell culture media, fetal bovine serum, bone marrow, organs, foods and cosmetics such as shampoos, lotions and creams. The products may be irradiated in various forms, including, solid, liquid and lyophilized forms.

What I claim as my invention is:

1. A method for sterilizing a biological product comprising irradiating the product with gamma irradiation at a rate of from about 0.25 kGy/hr. to about 20 kGy/hr. for a period of time sufficient to sterilize the product, wherein said biological product contains at least one biological material selected from the group consisting of: dextrose, antibodies, IgG, albumin, alpha 1 proteinase inhibitor, fibrinogen, Factor VII, Factor VIII, Factor IX, pharmaceuticals, nucleic acids, body fluids, saliva, cerebral spinal fluid, liposomes, glucose, cell culture media, fetal bovine serum, bone marrow and organs.

2. A method according to claim 1, wherein said irradiation is provided at a rate of from about 0.5 kGy/hr. to about 1.5 kGy/hr.

3. A method according to claim 1, wherein said irradiation is provided at a rate of from about 0.5 kGy/hr. to about 1.0 kGy/hr.

4. A method according to claim 1, wherein said product contains dextrose.

5. A method according to claim 1, wherein said biological product is an antibody.

6. A method according to claim 1, wherein said product is in lyophilized form.

7. A method according to claim 6, wherein said product is selected from the group consisting of IgG, albumin, alpha 1 proteinase inhibitor, fibrinogen, Factor VII, Factor VIII and Factor IX.

8. A method according to claim 1, wherein said product is selected from the group consisting of IgG, albumin, alpha 1 proteinase inhibitor, fibrinogen, Factor VII, Factor VIII and Factor IX.

9. A method for sterilizing a biological product comprising irradiating the product at ambient temperature or below with gamma irradiation at a rate of from about 0.1 kGy/hr. to about 3.0 kGy/hr. for a period of time sufficient to sterilize the product, wherein said biological product contains at least one biological material selected from the group consisting of: dextrose, antibodies, IgG, albumin, alpha 1 proteinase inhibitor, fibrinogen, Factor VII, Factor VIII, Factor IX, pharmaceuticals, nucleic acids, body fluids, saliva, cerebral spinal fluid, liposomes, glucose, cell culture media, fetal bovine serum, bone marrow and organs.

10. A method for sterilizing a biological product comprising irradiating the product with gamma irradiation at a rate of from about 0.1 kGy/hr. to about 3.0 kGy/hr for a period of time sufficient to sterilize the product, wherein said biological product contains at least one biological material selected from the group consist of: dextrose, antibodies, IgG, albumin, alpha 1 proteinase inhibitor, fibrinogen, Factor VII, Factor VIII, Factor IX, pharmaceuticals, nucleic acids, body fluids, saliva, cerebral spinal fluid, liposomes, glucose, cell culture media, fetal bovine serum, bone marrow and organs.

11. A method for sterilizing a biological product comprising irradiating the product with gamma irradiation at a rate of from about 0.1 kGy/hr. to about 3.0 kGy/hr. for a period of time greater than 10 hours, wherein said biological product contains at least one biological material selected from the group consisting of: dextrose, antibodies, IgG, albumin, alpha 1 proteinase inhibitor, fibrinogen, Factor VII, Factor VIII, Factor IX, pharmaceuticals, nucleic adds, body fluids, saliva, cerebral spinal fluid, liposomes, glucose, cell culture media, fetal bovine serum, bone marrow and organs.

12. The method according to one of claims 9, 10 or 11, wherein said irradiation is provided at a rate of from about 0.25 kGy/hr. to about 2.0 kGy/hr.

13. The method according to one of claims 9, 10 or 11, wherein said irradiation is provided at a rate of from about 0.5 kGy/hr. to about 1.5 kGy/hr.

14. The method according to one of claims 9, 10 or 11, wherein said irradiation is provided at a rate of from about 0.5 kGy/hr. to about 1.0 kGy/hr.

15. The method according to one of claims 9, 10 or 11, wherein said biological product comprises dextrose.

16. The method according to claim one of claims 9, 10 or 11, wherein said biological product is an antibody.

17. The method according to one of claims 9, 10 or 11, wherein said biological product is in lyophilized form.

18. The method according to one of claim 17, wherein said biological product is selected from the group consisting of IgG, albumin, alpha 1 proteinase inhibitor, fibrinogen, Factor VII, Factor VIII and Factor IX.

19. The method according to one of claims 9, 10 or 11, wherein said biological product is selected from the group consisting of IgG, albumin, alpha 1 proteinase inhibitor, fibrinogen, Factor VII, Factor VIII and Factor IX.

* * * * *